(12) United States Patent
Tsai

(10) Patent No.: US 10,245,430 B2
(45) Date of Patent: *Apr. 2, 2019

(54) SIGNAL PROCESSING METHOD FOR COCHLEAR IMPLANT

(71) Applicant: iMEDI PLUS Inc., Zhubei (TW)

(72) Inventor: Kun-Hsi Tsai, Zhubei (TW)

(73) Assignee: iMEDI PLUS Inc., Zhubei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,351

(22) Filed: Aug. 31, 2017

(65) Prior Publication Data

US 2017/0361098 A1 Dec. 21, 2017

Related U.S. Application Data

(62) Division of application No. 14/838,298, filed on Aug. 27, 2015, now Pat. No. 9,782,586.

(51) Int. Cl.
| | |
|---|---|
| *A61N 1/05* | (2006.01) |
| *A61N 1/36* | (2006.01) |
| *G10L 19/00* | (2013.01) |
| *G10L 21/0224* | (2013.01) |
| *H04R 25/00* | (2006.01) |
| *G10L 21/0208* | (2013.01) |
| *G10L 21/0324* | (2013.01) |

(52) U.S. Cl.
CPC ..... *A61N 1/36038* (2017.08); *A61N 1/36036* (2017.08); *G10L 19/00* (2013.01); *G10L 21/0224* (2013.01); *G10L 21/0208* (2013.01); *G10L 21/0324* (2013.01); *H04R 25/505* (2013.01); *H04R 2225/43* (2013.01); *H04R 2225/67* (2013.01); *H04R 2410/00* (2013.01)

(58) Field of Classification Search
CPC .............. A61N 1/0541; A61N 1/36032; H04R 25/353–25/356; H04R 25/502–25/505
See application file for complete search history.

(56) References Cited

U.S. PATENT DOCUMENTS

| | | | | |
|---|---|---|---|---|
| 7,027,987 B1 * | 4/2006 | Franz | ...................... | G10L 15/22 704/236 |
| 9,782,586 B2 * | 10/2017 | Tsai | ...................... | G10L 19/00 |
| 2004/0172242 A1 * | 9/2004 | Seligman | .............. | H04R 25/606 704/225 |
| 2005/0111683 A1 * | 5/2005 | Chabries | ................ | H03G 9/005 381/317 |
| 2009/0187065 A1 * | 7/2009 | Basinger | .............. | H04R 25/606 600/25 |

* cited by examiner

*Primary Examiner* — Eric D. Bertram

(74) *Attorney, Agent, or Firm* — Chieh-Mei Wang

(57) ABSTRACT

A signal processing method for cochlear implant is performed by a speech processor and comprises a noise reduction stage and a signal compression stage. The noise reduction stage can efficiently reduce noise in a electrical speech signal of a normal speech. The signal compression stage can perform good signal compression to enhance signals to stimulate cochlear nerves of a patient with hearing loss. The patient who uses a cochlear implant performing the signal processing method of the present disclosure can accurately hear normal speech.

9 Claims, 7 Drawing Sheets

SIGNAL PROCESSING METHOD FOR COCHLEAR IMPLANT

CROSS-REFERENCE TO RELATED APPLICATIONS

This application is a divisional application of U.S. patent application Ser. No. 14/838,298 filed on Aug. 27, 2015, now U.S. Pat. No. 9,782,586. The entire disclosure of the prior application is considered to be part of the disclosure of the accompanying application and is hereby incorporated by reference.

BACKGROUND

The present disclosure relates to a signal processing method, and more particularly to a signal processing method applied in cochlear implant.

Cochlear implant is a surgically implanted electronic device that provides a sense of sound to patients with hearing loss. Progress of the cochlear implant technologies has enabled many such patients to enjoy high quality level of speech understanding.

Noise reduction and signal compression are critical stages in the cochlear implant. For example, a conventional cochlear implant comprising multiple microphones can enhance the sensed speech volume. However, noise in the sensed speech is also amplified and compressed so as to affect the speech clarity. Besides, the multiple microphones increase hardware cost.

BRIEF DESCRIPTION OF THE DRAWINGS

The present disclosure is illustrated by way of embodiments and accompanying drawings.

DETAILED DESCRIPTION

Figure 1:
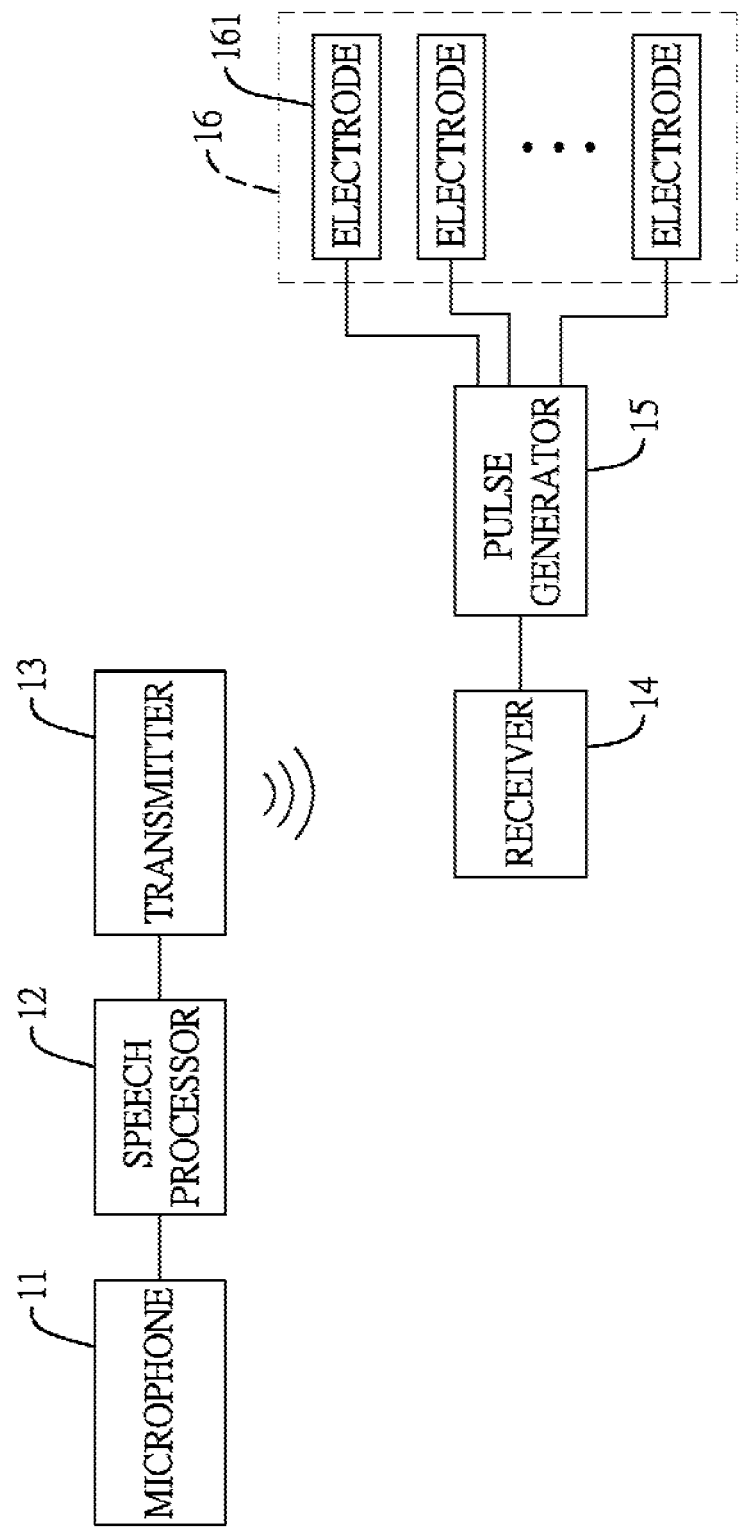
FIG. 1 is a circuit block diagram of a cochlear implant of a prior art.

With reference to FIG. 1, a basic and conventional configuration of a circuit block diagram of a cochlear implant comprises a microphone 11, a speech processor 12, a transmitter 13, a receiver 14, a pulse generator 15, and an electrode array 16. The microphone 11 and the speech processor 12 are assembled to be mounted on a patient's ear. The transmitter 13 is adapted to be attached on skin of the patient's head. The receiver 14, the pulse generator 15, and the electrode array 16 are implanted under the skin on head of a patient.

The microphone 11 is an acoustic-to-electric transducer that converts a normal speech sound into an electrical speech signal. The speech processor 12 receives the electrical speech signal and converts the electrical speech signal into multiple output sub-speech signals in different frequencies. The transmitter 13 receives the output sub-speech signals from the speech processor 12 and wirelessly sends the output sub-speech signals to the receiver 14. The pulse generator 15 receives the output sub-speech signals from the receiver 14 and generates different electrical pulses based on the output sub-speech signals to the electrode array 16. The electrode array 16 includes a plurality of electrodes 161 and each of the electrodes 161 electrically connected to different cochlear nerves of the patient's inner ear. The electrodes 161 output the electrical pulses to stimulate the cochlear nerves, such that the patient can hear something approximating to normal speech.

The present disclosure provides a signal processing method for cochlear implant and the cochlear implant using the same. The signal processing method is performed by a speech processor of the cochlear implant. The signal processing method is configured to compress an input speech signal into a predetermined amplitude range, which includes a noise reduction stage and a signal compression stage.

Figure 2:
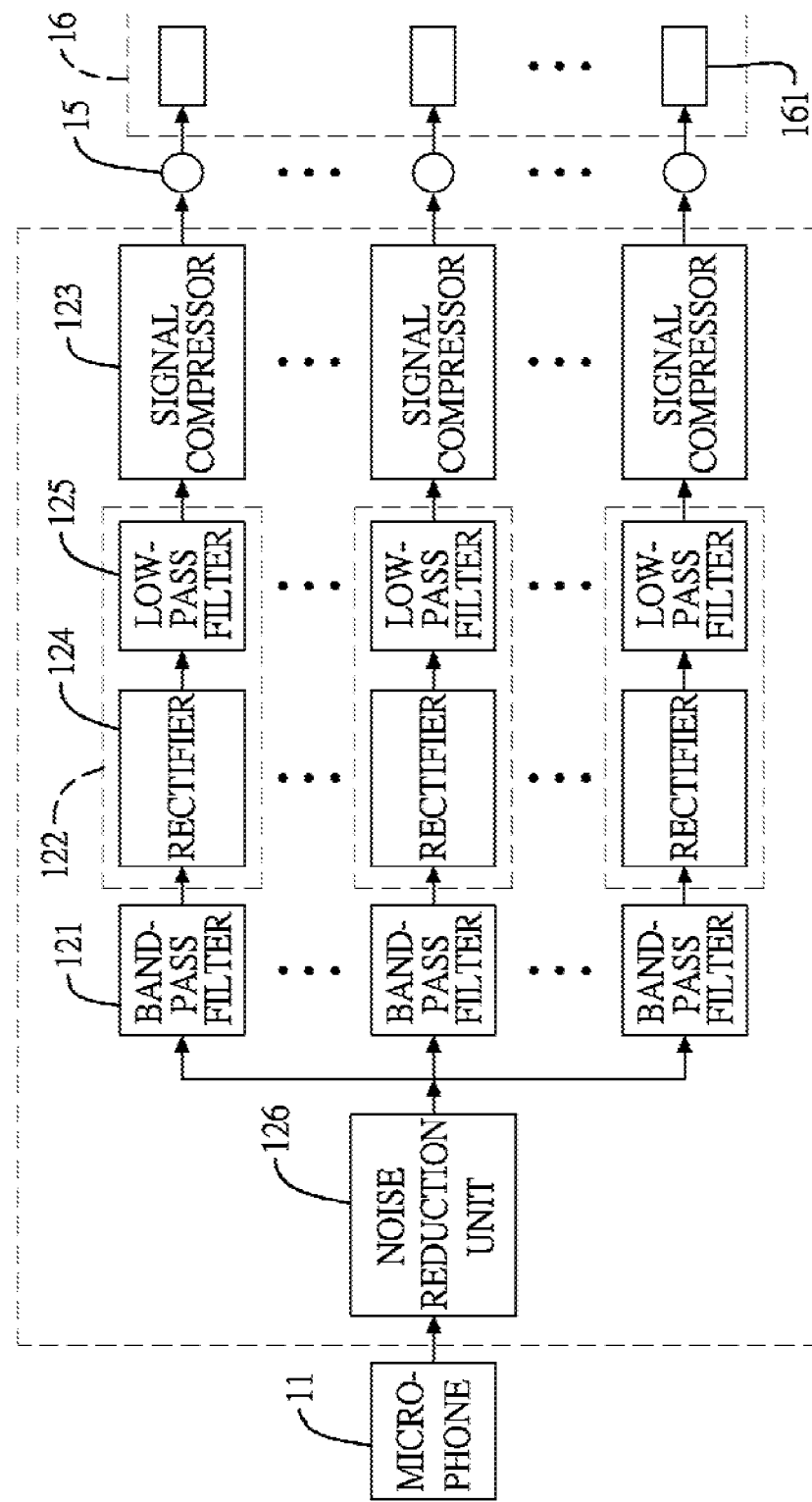
FIG. 2 is a detailed circuit diagram showing a speech processor connected to a microphone and pulse generators of an exemplary embodiment of the present disclosure.

In more detail, with reference to FIG. 2, the speech processor 12 has multiple channels including a first channel, a second channel, . . . , an i-th channel, . . . , and a n-th channel, wherein i and n are positive integers. Each one of the channels has a band-pass filter 121, an envelope detection unit 122, and a signal compressor 123. The envelope detection unit 122 is used to detect an amplitude envelope of a signal and can have a rectifier 124 and a low-pass filter 125. In the present disclosure, a noise reduction unit 126 is added. The noise reduction unit 126 is connected between the microphone 11 and the band-pass filters 121 of each one of the channels. In time domain, when the noise reduction unit 126 receives the electrical speech signal from the microphone 11, the noise reduction unit 126 segments the electrical speech signal into several continuous frames to reduce noise of the frames. For example, when a time length of the electrical speech signal is 3 seconds, the noise reduction unit 126 can segment the electrical speech signal into 300 continuous frames, wherein a time length of each one of the frames of the electrical speech signal is 10 milliseconds.

Based on the above configuration, the band-pass filter 121 of each one of the channels sequentially receives the frames of the electrical speech signal from the noise reduction unit 126. The band-pass filter 121 of each one of the channels can preserve elements of each one of the frames of the electrical speech signal within a specific frequency band and remove elements beyond the specific frequency band from such frame. The specific frequency bands of the band-pass filters 121 of the channels are different from each other. Afterwards, the amplitude envelopes of the frames of the electrical speech signal are detected by the envelope detection units 122 and are provided to the signal compressors 123.

The present disclosure relates to a noise reduction stage performed by the noise reduction unit 126 and a signal compression stage performed by the signal compressor 123. The noise reduction stage and the signal compression stage are described below.

1. Noise Reduction Stage

Figure 3:
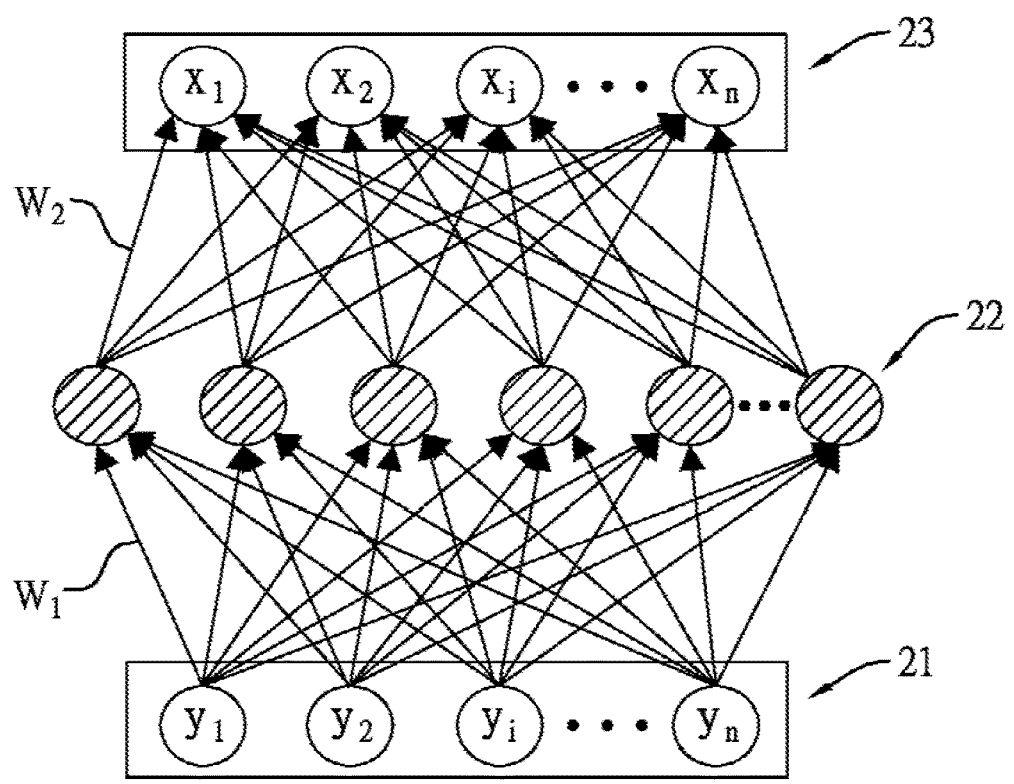
FIG. 3 is a schematic view of a single-layered DAE-based NR structure.

The noise reduction unit 126 can be performed in a deep denoising autoencoder (DDAE)-based noise reduction (NR) structure. The DDAE-based NR structure is widely used in building a deep neural architecture for robust feature extraction and classification. In brief, with reference to FIG. 3, a single-layered denoising autoencoder (DAE)-based NR structure comprises an input layer 21, a hidden layer 22, and an output layer 23. The DDAE-based NR structure is a multiple-layered DAE-based NR structure comprising the input layer 21, the output layer 23, and multiple hidden layers 22. Because the parameter estimation and speech enhancement procedure of DDAE is the same as for that of single-layered DAE, only the parameter estimation and speech enhancement for the single-layered DAE is presented, for ease of explanation. The same parameter estimation and speech enhancement procedures can be followed for the DDAE.

The input layer 21 receives an electrical speech signal y from the microphone 11 and segments the electrical speech signal y into a first noisy frame $y_1$, a second noisy frame $y_2, \ldots$, a t-th noisy frame $y_t, \ldots$, and a T-th noisy frame $y_T$, wherein T is a length of the current utterance. In other words, the present disclosure may segment an input speech signal, such as the electrical speech signal y, into a plurality of time-sequenced frames, such as the noisy frames $y_1, y_2, \ldots$, and $y_T$. For the elements in the t-th noisy frame $y_t$, the noise reduction unit 126 reduces noise in the t-th noisy frame $y_t$ to form a t-th clean frame $x_t$. Afterwards, the output layer 23 sends the t-th clean frame $x_t$ to the channels of the speech processor 12.

A relationship between the t-th noisy frame $y_t$ and the t-th clean frame $x_t$ can be represented as:

$$x_t = W_2 h(y_t) + b_2 \quad \text{(equation (1))}$$

wherein $h(y_t)$ is a function including $W_1$ and $b_1$ in time domain and $W_1$ and $W_2$ are default connection weights in time domain. $b_1$ and $b_2$ are default vectors of biases of the hidden layers 22 of the DDAE-based NR structure in time domain.

In another embodiment, the relationship between the t-th noisy frame $y_t$ and the t-th clean frame $x_t$ can be represented as:

$$x_t = \text{InvF}\{(W_2' h'(F\{y_t\}) + b_2')\} \quad \text{(equation (2))}$$

wherein $F\{\}$ is a Fourier transform function to transfer the t-th noisy frame $y_t$ from time domain to frequency domain and $h'(\ )$ is a function including $W_1'$ and $b_1'$; $W_1'$ and $W_2'$ are default connection weights in frequency domain. $b_1'$ and $b_2'$ are default vectors of biases of the hidden layers 22 of the DDAE-based NR structure in frequency domain and InvF $\{\ \}$ is an inverse Fourier transform function to obtain the t-th clean frame $x_t$.

According to experiment results, the t-th clean frame $x_t$ deduced from the Fourier transform and the inverse-Fourier transform as mentioned above has better performance than that without the Fourier transform and the inverse-Fourier transform.

For the time domain based method as shown in equation (1), $h(y_t)$ can be represented as:

$$h(y_t) = \sigma(W_1 y_t + b_1) = \frac{1}{1 + \exp[-(W_1 y_t + b_1)]} \quad \text{(equation (3))}$$

For the frequency domain based method shown in equation (2), $h'(F\{y_t\})$ can be represented as:

$$h'(F\{y_t\}) = \sigma(W_1' F\{y_t\} + b_1') = \frac{1}{1 + \exp[-(W_1' F\{y_t\} + b_1')]} \quad \text{(equation (4))}$$

Regarding the parameters including $W_1$, $W_2$, $b_1$ and $b_2$ in time domain or $W_1'$, $W_2'$, $b_1'$ and $b_2'$ in frequency domain, they are preset in the speech processor 12.

For example, in time domain, the parameters including $W_1$, $W_2$, $b_1$ and $b_2$ in equations (1) and (3) are obtained from a training stage. Training data includes a clean speech sample u and a corresponding noisy speech sample v. Likewise, the clean speech sample u is segmented into several clean frames $u_1, u_2, \ldots, u_{T'}$, and the noisy speech sample v is segmented into several noisy frames $v_1, v_2, \ldots, v_{T'}$, wherein T' is a length of a training utterance.

The parameters including $W_1$, $W_2$, $b_1$ and $b_2$ of equation (1) and equation (3) are optimized based on the following objective function:

$$\theta^* = \text{argmin}_\theta \left( \frac{1}{T'} \sum_{t=1}^{T'} \|u_t - \bar{u}_t\|_2^2 + \eta(\|W_1\|_2^2 + \|W_2\|_2^2) \right) \quad \text{(equation (5))}$$

In equation (5), θ is a parameter set $\{W_1, W_2, b_1, b_2\}$, T' is a total number of the clean frames $u_1, u_2, \ldots, u_{T'}$, and η is a constant used to control the tradeoff between reconstruction accuracy and regularization on connection weights (for example, η can be set as 0.0002). The training data including the clean frames $u_1, u_2, \ldots, u_{T'}$, and the training parameters of $W_{1\text{-}test}$, $W_{2\text{-}test}$, $b_{1\text{-}test}$ and $b_{2\text{-}test}$ can be substituted into the equation (1) and equation (3) to obtain a reference frame $\bar{u}_t$. When the training parameters of $W_{1\text{-}test}$, $W_{2\text{-}test}$, $b_{1\text{-}test}$, and $b_{2\text{-}test}$ can make the reference frame $\bar{u}_t$ be approximate to the clean frames $u_t$, such training parameters of $W_{1\text{-}test}$, $W_{2\text{-}test}$, $b_{1\text{-}test}$, and $b_{2\text{-}test}$ are taken as the parameters of $W_1$, $W_2$, $b_1$ and $b_2$ of equation (1) and equation (3). When the noisy speech sample v approximates the electrical speech signal y, the training result of the parameters of $W_1$, $W_2$, $b_1$ and $b_2$ can be optimized. The optimization of equation (5) can be done by using any unconstrained optimization algorithm. For example, a Hessian-free algorithm can be applied in the present disclosure.

After training, optimized parameters including $W_1$, $W_2$, $b_1$ and $b_2$ are obtained, to be applied to equation (1) and equation (3) for real noise reduction application.

In frequency domain, the parameters including $W_1'$, $W_2'$, $b_1'$ and $b_2'$ of equation (2) and equation (4) are optimized based on the following objective function:

$$\theta^* = \text{argmin}_\theta \left( \frac{1}{T'} \sum_{t=1}^{T'} \|u_t - \bar{u}_t\|_2^2 + \eta(\|W_1'\|_2^2 + \|W_2'\|_2^2) \right) \quad \text{(equation (6))}$$

In equation (6), θ is a parameter set $\{W_1', W_2', b_1', b_2'\}$, T' is a total number of the clean frames $u_1, u_2, \ldots, u_{T'}$, and η is a constant used to control the tradeoff between reconstruction accuracy and regularization on connection weights (for example, η can be set as 0.0002). The training data including the clean frames $u_1, u_2, u_{T'}$ and the training parameters of $W_{1\text{-}test}'$, $W_{2\text{-}test}'$, $b_{1\text{-}test}'$ and $b_{2\text{-}test}'$ can be substituted into the equation (2) and equation (4) to obtain a reference frame $\bar{u}_t$. When the training parameters of $W_{1\text{-}test}'$, $W_{2\text{-}test}'$, $b_{1\text{-}test}'$ and $b_{2\text{-}test}'$ can make the reference frame $\bar{u}_t$ be approximate to the clean frames $u_t$, such training parameters of $W_{1\text{-}test}'$, $W_{2\text{-}test}'$, $b_{1\text{-}test}'$ and $b_{2\text{-}test}'$ are taken as the parameters of $W_{1\text{-}test}'$, $W_{2\text{-}test}'$, $b_{1\text{-}test}'$ and $b_{2\text{-}test}'$ of equation (2) and equation (4). When the noisy speech sample v approximates the electrical speech signal y, the training result of the parameters of $W_1'$, $W_2'$, $b_1'$ and $b_2'$ can be optimized. The optimization of equation (6) can be done by using any unconstrained optimization algorithm. For example, a Hessian-free algorithm can be applied in the present disclosure.

After training, optimized parameters including $W_1'$, $W_2'$, $b_1'$ and $b_2'$ are obtained, to be applied to equation (2) and equation (4) for real noise reduction application.

Figure 4A:
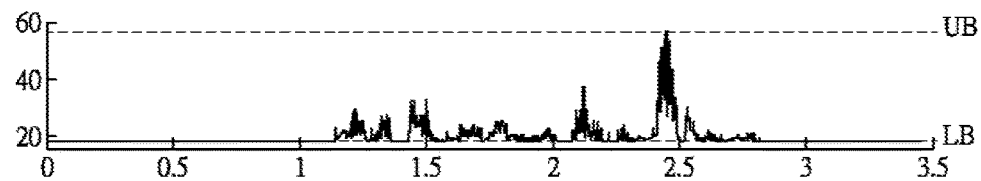
FIG. 4A shows an amplitude envelope of a clean speech signal.
Figure 4B:
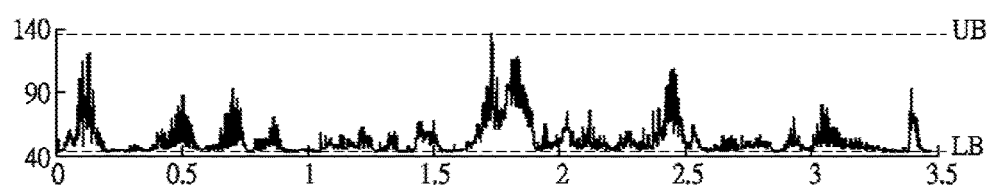
FIG. 4B shows an amplitude envelope of a noisy speech signal.
Figure 4C:
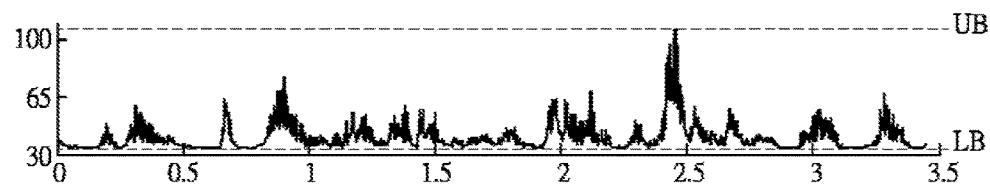
FIG. 4C shows an amplitude envelope detected by a conventional log-MMSE estimator.
Figure 4D:
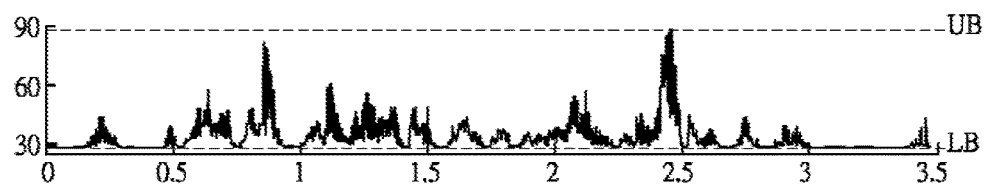
FIG. 4D shows an amplitude envelope detected by a conventional KLT estimator.
Figure 4E:
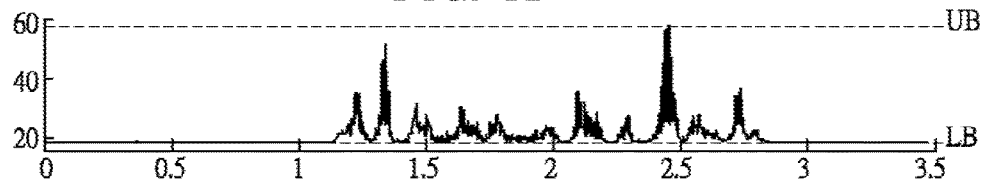
FIG. 4E shows an amplitude envelope detected by the exemplary embodiment of the present disclosure.

With reference to FIGS. 4A and 4B, FIG. 4A an amplitude envelope of a clean speech signal is shown and FIG. 4B shows an amplitude envelope of a noisy speech signal. FIG. 4C shows an amplitude envelope detected by a conventional log-MMSE (minimum mean square error) estimator. FIG. 4D shows an amplitude envelope detected by a conventional KLT (Karhunen-Loeve transform) estimator. FIG. 4E shows an amplitude envelope detected by the present disclosure. Comparing FIG. 4E with FIG. 4A, the result of detection is most closely approximate to the clean speech signal, which means the noise is removed. Comparing FIG. 4B with FIGS. 4C and 4D, the results of detection as illustrated in FIGS. 4C and 4D are still noisy.

According to experiment result as mentioned above, the signal performances of the conventional log-MMSE estimator and the KLT estimator are not as good as those obtained by the procedures of the present disclosure. The procedures of the present disclosure have better noise reducing efficiency.

2. Signal Compression Stage

Figure 5:
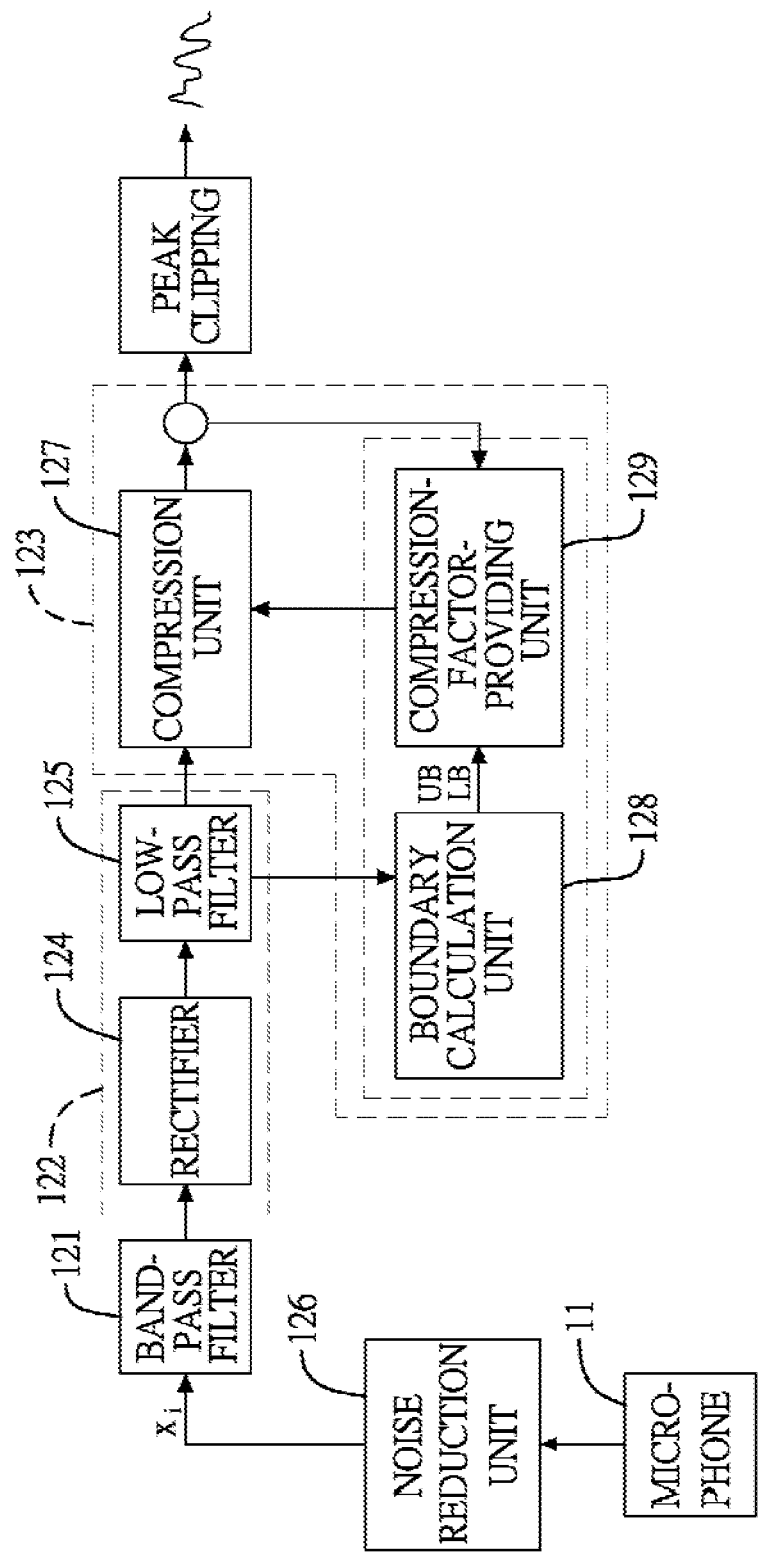
FIG. 5 is a circuit block diagram of one channel of the speech processor of FIG. 2.
Figure 6:
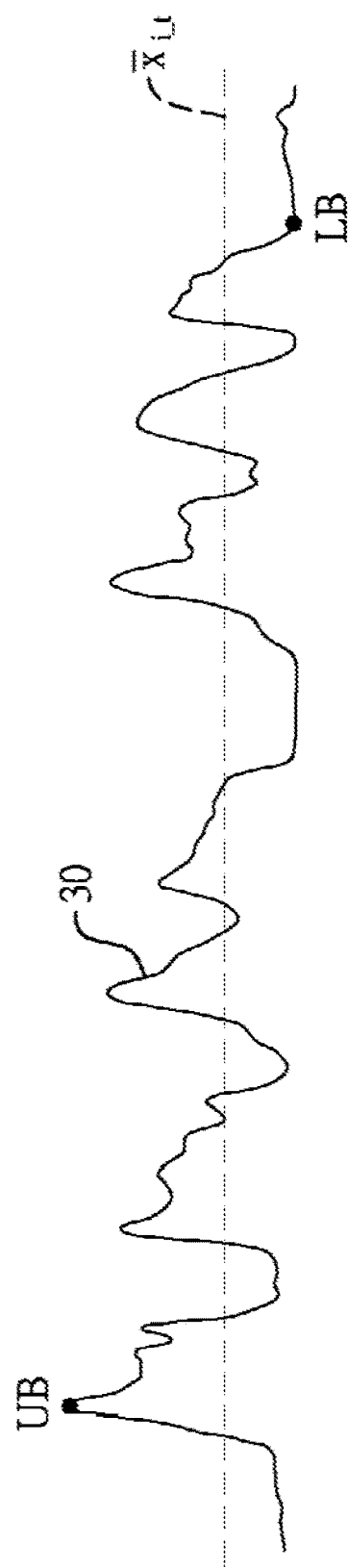
FIG. 6 is a waveform diagram of an amplitude envelope detected by an envelope detection unit of the speech processor of FIG. 2.

With reference to FIGS. 2 and 5, for the i-th channel of the speech processor 12, the signal compressor 123 receives an amplitude envelope of the t-th clean frame $x_t$ within the specific frequency band from the noise reduction unit 126, through the band-pass filter 121 and the envelope detection unit 122. The amplitude envelope 30 of the t-th clean frame $x_t$ is illustrated in FIG. 6. As shown in FIG. 6, the amplitude envelope 30 of t-th clean frame $x_t$ is time-varying.

The signal compressor 123 of the present disclosure comprises a compression unit 127, a boundary calculation unit 128, and a compression-factor-providing unit 129. The compression unit 127 and the boundary calculation unit 128 are connected to the envelope detection unit 122 to receive the amplitude envelope 30 of the t-th clean frame $x_t$ in real-time. With reference to FIGS. 5 and 6, the boundary calculation unit 128 can detect an upper boundary UB and a lower boundary LB in the amplitude envelope of the t-th clean frame $x_t$. The results of calculations as to the upper boundary UB and the lower boundary LB are transmitted to the compression-factor-providing unit 129. The upper boundary UB and the lower boundary LB can be calculated by:

$$UB = \bar{x}_t + \alpha_0 \times (\max(x_t) - \bar{x}_t) \quad \text{(equation (7))}$$

$$LB = \bar{x}_t + \alpha_0 \times (\min(x_t) - \bar{x}_t) \quad \text{(equation (8))}$$

wherein $\alpha_0$ is an initial value.

The compression unit 127 receives the amplitude envelope 30 of the t-th clean frame $x_t$ and outputs a t-th output frame $z_t$. Inputs of the compression-factor-providing unit 129 are connected to an input of the compression unit 127, an output of the compression unit 127, and an output of the boundary calculation unit 128. Results of calculating the upper boundary UB, the lower boundary LB, and the t-th output frame $z_t$ are received from unit 128. An output of the compression-factor-providing unit 129 is connected to the input of the compression unit 127, such that the compression-factor-providing unit 129 provides a compression factor $\alpha_t$ to the compression unit 127. The compression factor $\alpha_t$ is determined according to a previous compression factor $\alpha_{t-1}$, the upper boundary UB, the lower boundary LB, and the t-th output frame $z_t$. In brief, the procedures herein may determine the compression factor $\alpha_t$ for a frame based on the frame's amplitude upper boundary UB and lower boundary LB. When the t-th output frame $z_t$ is in a monitoring range between the upper boundary UB and the lower boundary LB, the compression factor $\alpha_t$ can be expressed as:

$$\alpha_t = \alpha_{t-1} + \Delta\alpha_1 \quad \text{(equation (9))}$$

where $\Delta\alpha_1$ is a positive value (i.e., $\Delta\alpha_1 = 1$).

In contrast, when the t-th output frame $z_t$ is beyond the monitoring range, the compression factor $\alpha_t$ can be expressed as:

$$\alpha_t = \alpha_{t-1} + \Delta\alpha_2 \quad \text{(equation (10))}$$

where $\Delta\alpha_2$ is a negative value (i.e., $\Delta\alpha_2 = -0.1$).

The t-th output frame $z_t$ can be expressed as:

$$z_t = \alpha_t \times (x_t - \bar{x}_t) + \bar{x}_t \quad \text{(equation (11))}$$

where $\bar{x}_t$ is a mean of the amplitude envelope of the t-th clean frame $x_t$.

Figure 7:
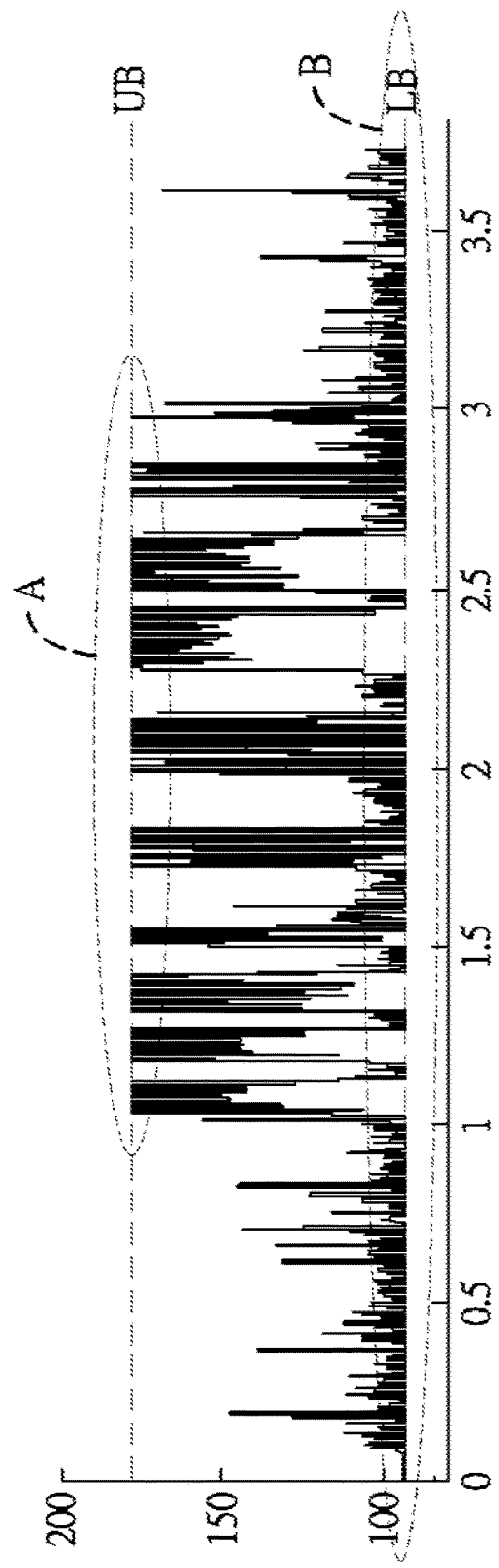
FIG. 7 is a waveform diagram of an output frame generated by the signal compressor of the speech processor of FIG. 2.

According to equations (9) and (10), a present compression factor $\alpha_t$ is obtained by a previous compression factor $\alpha_{t-1}$. It can be understood that the compression factor $\alpha_t$ for the next frame can be modified based on the next frame's amplitude upper boundary UB and lower boundary LB. According to equation (11), the t-th output frame $z_t$ is repeatedly adjusted by the t-th clean frame $x_t$ and the results of calculating UB, LB, and $\alpha_t$. According to experiment result, the signal compression capability is good. As illustrated in FIG. 7, speech components A in the t-th output frame $z_t$ are amplified. The speech components A even reach the upper boundary UB. In contrast, noise components B are not significantly amplified. Therefore, the t-th output frame $z_t$ is enhanced to stimulate the cochlear nerves and the patient can accurately hear a spoken conversation.

What is claimed is:

1. A signal processing method for a cochlear implant, the cochlear implant comprising a microphone and a speech processor, the signal processing method being executed by the speech processor comprising:
    receiving an electrical speech signal from the microphone;
    segmenting the electrical speech signal to a plurality of time-sequenced noisy frames;
    reducing noise in each of the plurality of time-sequenced signal frames to obtain a plurality of clean signal frames, the plurality of clean signal frames comprising a (t-1)-th clean frame $x_{t-1}$ and a t-th clean frame $x_t$;
    obtaining a (t-1)-th compression factor $\alpha_{t-1}$ according to the (t-1)-th clean frame $x_{t-1}$;
    obtaining a t-th compression factor $\alpha_t$ for the t-th clean frame $x_t$ according to the compression factor $\alpha_{t-1}$ and the t-th clean frame $x_t$;
    obtaining a t-th output frame $z_t$ based on the t-th compression factor $\alpha_t$; and
    outputting the t-th output frame $z_t$.

2. The signal processing method of claim 1, further comprising:

obtaining a (t-1)-th amplitude envelope of the (t-1)-th clean frame $x_{t-1}$ and calculating a (t-1)-th upper boundary and a(t-1)-th lower boundary of the (t-1)-th amplitude envelope;

wherein the (t-1)-th compression factor $\alpha_{t-1}$ for the (t-1)-th clean frame $x_{t-1}$ is obtained based on the (t-1)-th upper boundary and the (t-1)-th lower boundary.

3. The signal processing method of claim 2, further comprising:

obtaining a t-th amplitude envelope of the t-th clean frame $x_t$ and calculating a t-th upper boundary and a t-th lower boundary of the t-th amplitude envelope;

wherein the t-th compression factor $\alpha_t$ for the t-th clean frame $x_t$ is obtained based on the compression factor $\alpha t-1$, the t-th upper boundary and the t-th lower boundary.

4. The signal processing method of claim 3, wherein when the t-th output frame zt falls within a range between a the t-th upper boundary and the t-th lower boundary, the t-th compression factor $\alpha t$ is calculated by: $\alpha t = \alpha t-1 + \Delta\alpha 1$, and $\Delta\alpha 1$ is a positive value.

5. The signal processing method of claim 3, wherein when the t-th output frame $z_t$ falls beyond a range between a the t-th upper boundary and the t-th lower boundary, the t-th compression factor $\alpha_t$ is calculated by: $\alpha_t = \alpha_{t-1} + \Delta\alpha_2$, and $\Delta\alpha_2$ is a negative value.

6. The signal processing method of claim 1, wherein the t-th output frame $z_t$, is obtained by: $z_t = \alpha_t \times (x_t - \bar{x}_t) + \bar{x}_t$, and $\bar{x}_t$ is a mean of the t-th amplitude envelope of the t-th clean frame $x_t$.

7. The signal processing method of claim 1, wherein the t-th clean frame $x_t$ is calculated by:

$$x_t = InvF\{(W_2'h'(F\{y_t\}) + b_2')\}$$

wherein $F\{\}$ is a Fourier transform function to transfer the t-th noisy frame $y_t$ from time domain to frequency domain;

$h'(\ )$ is a function including $W_1'$ and $b_1'$;

$W_1'$ and $W_2'$ are default connection weights in frequency domain;

$b_1'$ and $b_2'$ are default vectors of biases of hidden layers of a DDAE-based NR structure in the frequency domain; and $InvF\{\ \}$ is an inverse Fourier transform function.

8. The signal processing method of claim 7, wherein the $h'(F\{y_t\})$ is calculated by:

$$h'(F\{y_t\}) = \frac{1}{1 + \exp[-(W_1'F\{y_t\} + b_1')]}.$$

9. The signal processing method of claim 1, wherein the t-th upper boundary (UB) is calculated by $UB = \bar{x}_t + \alpha_0 \times (\max(x_t) - \bar{x}_t)$, the t-th lower boundary (LB) is calculated by $LB = \bar{x}_t + \alpha_0 \times (\max(x_t) - \bar{x}_t)$, and $\bar{x}_t$ is a mean of the t-th amplitude envelope of the t-th clean frame $x_t$.

* * * * *